United States Patent
Imbimbo

(10) Patent No.: US 9,592,210 B2
(45) Date of Patent: Mar. 14, 2017

(54) 1-PHENYLALKANECARBOXYLIC ACID DERIVATIVES FOR THE TREATMENT OF COGNITIVE IMPAIRMENT

(71) Applicant: Chiesi Farmaceutici S.p.A., Parma (IT)

(72) Inventor: Bruno Pietro Imbimbo, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/723,662

(22) Filed: Dec. 21, 2012

(65) Prior Publication Data
US 2013/0165505 A1 Jun. 27, 2013

Related U.S. Application Data

(60) Provisional application No. 61/579,312, filed on Dec. 22, 2011.

(51) Int. Cl.
*A61K 31/192* (2006.01)

(52) U.S. Cl.
CPC .................. *A61K 31/192* (2013.01)

(58) Field of Classification Search
CPC .................................................. A61K 31/192
See application file for complete search history.

(56) References Cited

U.S. PATENT DOCUMENTS

| | | | |
|---|---|---|---|
| 7,531,692 B2 | 5/2009 | Raveglia et al. | |
| 7,662,995 B2 | 2/2010 | Raveglia et al. | |
| 8,022,250 B2 | 9/2011 | Raveglia et al. | |
| 8,076,505 B2 | 12/2011 | Folleas et al. | |
| 2011/0039934 A1 | 2/2011 | Pivetti et al. | |
| 2011/0245346 A1 | 10/2011 | Pivetti et al. | |
| 2011/0263711 A1 | 10/2011 | Imbimbo et al. | |
| 2012/0022163 A1 | 1/2012 | Imbimbo et al. | |

OTHER PUBLICATIONS

Petersen et al., Arch Neurol. Dec. 2009; 66(12): 1447-1455.*
Butterfield et al., Free Radical Biology & Medicine 43 (2007) 658-677.*
Christensen et al (BMC Geriatrics 2008, 8:14).*
Dickerson et al (Neurology. Aug. 9, 2005; 65(3): 404-411).*
CNDAC (http://www.brain.northwestern.edu/pdfs/Disease%20Summaries/mci.pdf, accessed Apr. 26, 2016).*
Clinical Trial (https://clinicaltrials.gov/show/NCT01602393, accessed Apr. 26, 2016).*
Clinical Trail 2 (https://clinicaltrials.gov/show/NCT01421056, accessed Apr. 26, 2016).*
R. C. Petersen, *Lancet Neurol.*, vol. 12, pp. 933-935 (2013).
U.S. Appl. No. 14/460,821, filed Aug. 15, 2014, Imbimbo, et al.
V. Porrini et al., "CHF5074, in Clinical Development for Treatment and Prevention of Alzheimer's Disease, Switches Cultured Microglia from M1 to M2 Activation State," 11th International Conference on Alzheimer and Parkinson Diseases, Florence, Italy, Mar. 6-10, 2013.
J.S. Ross et al., "Sustained Cognitive Benefit in Patients with Mild Cognitive Impairment (MCI) Upon Prolonged Treatment with CHF5074," 16th Alzheimer's Association International Conference, Boston, Jul. 13-18, 2013.
Tifratene, et al., Neurology, vol. 85, pp. 331-338 (2015).
J. Ross, et al., Current Alzheimer Research, vol. 10, pp. 742-753 (2013).
16th Alzheimer's Association International Conference, Boston, Jul. 13-18, 2013, Abstract Mar. 6, 2005.
17th Alzheimer's Association International Conference, Copenhagen, Jul. 12-17, 2014, Abstract Apr. 11, 2001.
Alzheimer's Association Press Release, Jul. 2013.
U.S. Appl. No. 14/719,784, filed May 22, 2015, Imbimbo, et al.
R. Roberts, et al., Clin. Geriatr. Med., vol. 29 (2013).
S. L. Tyas, et al., Am. J. Epidemiol., vol. 165, pp. 1231-1238 (2007).
T. D. Koepsell, et al., Neurology, vol. 79, pp. 1591-1598 (2012).
A. J. Mitchell, et al., Acta Psychiatr. Scand., vol. 119, pp. 252-265 (2009).
O. V. Forlenza, et al., BMC Medicine, vol. 8 (2010).
R. C. Petersen, et al., NEJM, vol. 352, pp. 2379-2388 (2005).
R. J. Caselli et al., NEJM, vol. 361, pp. 255-263 (2009).

* cited by examiner

*Primary Examiner* — Savitha Rao
*Assistant Examiner* — Angela Brown-Pettigrew
(74) *Attorney, Agent, or Firm* — Oblon, McClelland, Maier & Neustadt, L.L.P.

(57) ABSTRACT

Administration of certain 1-phenylalkanecarboxylic acid derivatives is useful for improving Cognitive Function; treating Cognitive Impairment, in particular Mild Cognitive Impairment; and preventing and/or reducing the risk of developing Alzheimer's Disease in a cognitively normal subject.

8 Claims, No Drawings

1-PHENYLALKANECARBOXYLIC ACID DERIVATIVES FOR THE TREATMENT OF COGNITIVE IMPAIRMENT

CROSS REFERENCES TO RELATED APPLICATIONS

This application claims priority to U.S. Provisional Patent Application No. 61/579,312, filed on Dec. 22, 2011, which is incorporated herein by reference in its entirety.

BACKGROUND OF THE INVENTION

Field of the Invention

The present invention relates to the field of pharmacotherapy of cognitive deficits in learning and memory. More particularly, the invention relates to methods for improving Cognitive Function. The present invention also relates to methods for preventing and/or treating Cognitive Impairment, in particular Mild Cognitive Impairment. The present invention further relates to methods for preventing and/or reducing the risk of developing Alzheimer's Disease in a cognitively normal subject.

Discussion of the Background

Cognitive brain disorders are characterized clinically by progressive loss of memory, cognition, reasoning, executive functioning, planning, judgment and emotional stability, gradually leading to profound mental deterioration. A wide range of disorders can lead to disturbances of cognition. Neuropsychological cognitive deficits are common in people with functional neuropsychiatric disorders such as schizophrenia. Brain disorders characterized by cognition deficits are also those associated with progressive neuronal degeneration, such as dementia, Alzheimer's Disease Parkinson's Disease, Huntington's Disease, and multiple sclerosis (MS).

Alzheimer's disease (AD) is the most common form of dementia. The basic pathological abnormalities in AD brains are amyloid plaques, neurofibrillary tangles and neuronal loss. Amyloid plaques are composed of β-amyloid peptides (Aβ) that are proteolytically produced from amyloid precursor protein (APP). APP is initially cleaved by β-secretase to generate a 99-residue carboxy-terminal fragment (CTFβ or C99) that is subsequently cleaved by γ-secretase to generate Aβ. Proteolysis by γ-secretase is heterogeneous and generates several Aβ species of different lengths. The most abundant species is a 40-residue peptide (Aβ40). A 42-residue variant (Aβ42) is also formed and, although is much less abundant than Aβ40, is more prone to fibril formation and is the initially and predominantly deposited Aβ species in AD brains. Gamma-secretase is a complex of four different membrane proteins: presenilin (PS), nicastrin, anterior pharynx-defective (Aph-1), and presenilin enhancer 2 (Pen-2). Presenilins are of exceptional pathophysiological importance since more than 150 autosomal dominant point mutations are known in these proteins, all of which cause aggressive and early-onset AD. Many point mutations of APP and PS result in increased production of Aβ42 and according to the so called "amyloid hypothesis," the oligomeric forms of Aβ42 are the main cause of neuronal death in AD (see Lesné S, et al., Nature, 440: 352-357 (2006) and Shankar G M, et al., Nat. Med., 14: 837-842 (2008), both of which are incorporated herein by reference in their entireties). Thus, inhibition or modulation of γ-secretase appears to be a logical strategy to decrease Aβ42 accumulation in AD patients.

While a number of highly potent inhibitors of γ-secretase have been identified (see Olson R E, et al., Curr. Top. Med. Chem., 8: 17-33 (2008), which is incorporated herein by reference in its entirety), serious concerns about their toxicity have been raised since γ-secretase can cleave several other membrane proteins other than APP (see Lleo A, Curr. Top. Med. Chem., 8: 9-16 (2008), which is incorporated herein by reference in its entirety), the most pharmacologically relevant being the Notch receptor. Indeed, γ-secretase inhibitors block proteolysis of Notch by inhibiting cleavage at site 3 (see Lewis H D, et al., Biochemistry, 42: 7580-7586 (2003), which is incorporated herein by reference in its entirety). Physiological cleavage of Notch leads to release of the Notch intracellular domain (NICD), a protein fragment that is translocated to the nucleus where it regulates transcription of target genes involved in cell development and in differentiation of adult self-renewing cells. The inhibitory effects of γ-secretase inhibitors on Notch activation in embryonic and fetal development may not be of concern for the treatment of AD patients. However, it is known that Notch signaling plays an important role in the ongoing differentiation processes of the immune system (see Maillard I, et al., Immunity, 19: 781-791 (2003), which is incorporated herein by reference in its entirety), gastrointestinal tract (see Stanger B Z, et al., Proc. Natl. Acad. Sci. USA, 102: 12443-12448 (2005), which is incorporated herein by reference in its entirety) and epidermal differentiation process (see Panelos J, et al., Cancer Biol. Ther., 8: 1986-1993 (2009), which is incorporated herein by reference in its entirety). Indeed, treatment of mice with γ-secretase inhibitors can cause severe gastrointestinal toxicity and compromise the proper maturation of B- and T-lymphocytes (see Searfoss G H, et al., J. Biol. Chem., 278: 46107-46116 (2003) and Wong G T, et al., J. Biol. Chem., 279: 12876-12882 (2004), both of which are incorporated herein by reference in their entireties).

Recently, in two large 21-month Phase 3 trials conducted in more than 2,600 AD patients, an increased rate of skin cancer with semagacestat, a potent γ-secretase inhibitor, compared to placebo has been observed (see Eli Lilly and Company (2010), Lilly halts development of semagacestat for Alzheimer's disease based on preliminary results of Phase III clinical trials. Press Release Aug. 17, 2010, which is incorporated herein by reference in its entirety). In addition, an interim analysis of these two Phase 3 trials showed that cognition and the ability to complete activities of daily living of patients treated with semagacestat worsened over time to a statistically significantly higher rate than those treated with placebo (see Eli Lilly and Company (2010), Lilly halts development of semagacestat for Alzheimer's disease based on preliminary results of Phase III clinical trials. Press Release Aug. 17, 2010, which is incorporated herein by reference in its entirety). The reasons for the detrimental cognitive and functional effects of semagacestat in AD patients are unclear. The drug-induced accumulation in the brain of the neurotoxic C-terminal fragment of APP (CTFβ or C99) resulting from the γ-secretase block (see Gitter B D, et al., Neurobiol, Aging, 25 (Suppl 2): 5571 (2004), which is incorporated herein by reference in its entirety) and the tendency of the drug to increase brain (see Lanz T A, et al., J. Pharmacol. Exp. Ther., 319: 924-933 (2006), which is incorporated herein by reference in its entirety) and CSF (see Bateman R J, et al. Ann. Neurol., 66: 48-54 (2009), which is incorporated herein by reference in its entirety) levels of the neurotoxic Aβ42 peptide could play a role (see Imbimbo B P, et al., Curr. Opin. Investig. Drugs, 10: 721-730 (2009), which is incorporated herein by reference in its entirety). Indeed, semagacestat has been shown to decrease dendritic spine density in mice (see Bittner T, et al., *J. Neurosci.*, 2009; 29: 10405-10409 (2009), which is incorporated herein by reference in its entirety). Thus, in order to get safe and effective anti-AD drugs, Aβ42 may need to be selectively lowered without inducing abnormal accumulation of CTFβ and without affecting the proteolysis of Notch. This can be realized by modulating rather than inhibiting γ-secretase.

The first compounds of this type are certain non-steroidal anti-inflammatory drugs (NSAIDs) that are capable of altering the cleavage properties of γ-secretase to lower the production of Aβ42 and increase the formation of a shorter 38-residue species (Aβ38) (see Weggen S, et al., *Nature,* 414: 212-216 (2001), which is incorporated herein by reference in its entirety). These compounds include ibuprofen, sulindac sulfide, indomethacin, flurbiprofen, and others. The ability of these NSAIDs to modulate Aβ production is not related to their inhibitory activity on cyclooxygenase (COX). Binding of these NSAIDs to APP is more efficient than to Notch and thus their effects on Notch processing are minor (see Kukar T, et al., *Curr. Top. Med. Chem.*, 8: 47-53 (2008), which is incorporated herein by reference in its entirety). These NSAIDs are not very potent toward lowering Aβ production and structural modifications of these molecules have been proposed (see Peretto I, et al., *Curr. Top. Med. Chem.*, 8: 38-46 (2008), which is incorporated herein by reference in its entirety).

Certain new γ-secretase modulators endowed with selective Aβ42-lowering properties but devoid of COX inhibitory activity, thus suitable for chronic use in AD patients, have been reported (see Peretto I, et al., *J. Med. Chem.*, 48: 5705-5720 (2005), which is incorporated herein by reference in its entirety). Within this new chemical series, 1-(3', 4'-dichloro-2-fluorobiphenyl-4-yl)cyclopropanecarboxylic acid (CHF 5074) proved to be of major interest. In human neuroglioma cells over-expressing the Swedish mutated APP (H4swe), CHF 5074 preferentially lowers Aβ42 secretion with an $IC_{50}$ of 3.6 µM (see Imbimbo B P, et al., *J. Pharmacol. Exp. Ther.*, 323: 822-830 (2007), which is incorporated herein by reference in its entirety). CHF 5074 does not display inhibitory activity on COX-1 and COX-2 enzymes when employed at concentrations up to 100 µM and 300 µM, respectively (see Imbimbo B P, et al. *Pharmacol. Res.*, 55: 318-328 (2007), which is incorporated herein by reference in its entirety). At 5 µM, no effects were observed on Notch intracellular cleavage in human embryonic kidney 293 swe cells (see Imbimbo B P, et al., *J. Pharmacol. Exp. Ther.*, 323: 822-830 (2007), which is incorporated herein by reference in its entirety). At 100 µM, CHF 5074 does not alter the expression profile of several NICD-responsive genes (see Imbimbo B P, et al., *Pharmacol. Res.*, 55: 318-328 (2007), which is incorporated herein by reference in its entirety). In mice and rats, CHF 5074 appears to be well absorbed orally (74% and 50%, respectively) and slowly eliminated from plasma ($t_{1/2}$=12 and 20 hours, respectively) (see Peretto I, et al., *J. Med. Chem.*, 48: 5705-5720 (2005), which is incorporated herein by reference in its entirety). CHF 5074 brain levels represent 3-14% of the corresponding plasma concentrations. In guinea-pigs, CHF 5074 shows a prolonged plasma elimination half-life ($t_{1/2}$≈30 hours) after oral administration and a brain penetration of 3-9%. In dogs, the drug is quantitatively absorbed by oral route (80-100%) and is eliminated slowly from plasma ($t_{1/2}$≈24 hours). Brain to plasma drug levels range between 5 and 7%. The main metabolite of CHF 5074 appears to be the glucuronide conjugated derivative.

Pharmacological studies in transgenic mouse models of AD have shown that CHF 5074 is active from neuropathological and behavioral points of view at oral doses of 60 mg/kg/day (see Imbimbo B P, et al., *J. Pharmacol. Exp. Ther.*, 323: 822-830 (2007); Imbimbo B P, et al., *Br. J. Pharmacol.*, 159: 982-993 (2008); and Imbimbo B P, et al., *J. Alzheimers Dis.*, 20: 159-173 (2010), all of which are incorporated herein by reference in their entireties). At this dose level, the drug appears to be well tolerated by mice even after prolonged treatment for 4-9 months.

More in general, across several pathological conditions, an increasing number of patients are being identified who do not meet the diagnostic criteria for dementia but nonetheless have significant memory or cognitive impairment, defined as Mild Cognitive Impairment. Alzheimer's disease (AD) is the result of long-term pathophysiologic processes starting years before the onset of clinical symptoms. Therapeutic interventions should thus be started early on in the disease course so that patients can achieve the maximum benefit. Interest has therefore focused on identifying signs of cognitive decline as early as possible in the evolution of the disease. Several attempts have been made to characterize the cognitive impairment without dementia commonly seen in elderly individuals (see Ritchie K, et al., *Lancet;* 355: 225-228 (2000), which is incorporated herein by reference in its entirety). Mild cognitive impairment (MCI) is one of several concepts describing a cognitive state between normal aging and dementia: "MCI is a syndrome defined as cognitive decline greater than that expected for an individual's age and education level but that does not interfere notably with activities of daily living [ADL]" (see Gauthier S, et al., *Lancet,* 367: 1262-1270 (2006), which is incorporated herein by reference in its entirety). Subjects with MCI are at increased risk to develop dementia. Although "there is no agreement in the field on a single set of criteria for MCI" (see Petersen R C, et al., *J. Intern. Med.*, 256: 183-194 (2004), which is incorporated herein by reference in its entirety), criteria for MCI proposed in 1999 by investigators at Mayo Clinic (see Petersen R C, et al., *Arch. Neurol.*, 56: 303-308 (1999) and Petersen R C, et al., *Arch. Neurol.*, 66: 1447-1455 (2009), both of which are incorporated herein by reference in their entireties) have been largely used in clinical studies since then:

1) Memory complaint, preferably corroborated by an informant;

2) Memory impairment documented according to appropriate reference values;

3) Essentially normal performance in non-memory cognitive domains;

4) Generally preserved activities of daily living;

5) Not demented.

In the case of non-amnestic MCI patients, criterium 2 of the original Petersen et al's criteria (see Petersen R C, et al., *Arch. Neurol.*, 56: 303-308 (1999), which is incorporated herein by reference in its entirety) is also integrated with the diagnostic decision process suggested by Petersen (see Petersen R C, et al., *J. Intern. Med.*, 256: 183-194 (2004), which is incorporated herein by reference in its entirety): "Once the clinician has determined that the person is neither normal nor demented" but memory is not impaired, the other cognitive functions will be assessed to determine if the impairment involves other nonmemory domains.

Thus, Mild Cognitive Impairment (MCI) is a condition characterized by mild recent memory loss without dementia or significant impairment of other cognitive functions to an extent that is beyond that expected for age or educational background. Criteria for diagnosis of MCI are: memory complaint; abnormal activities of daily living; abnormal general cognitive functioning; abnormal memory for age; not demented.

The number of patients falling in the categories of MCI, Age-Associated Memory Impairment, Age-Related Cognitive Decline or similar diagnostic categories is staggering. For example, according to the estimates of Barker et al., *Br. J. Psychiatry*, 167(5):642-8 (1995), which is incorporated herein by reference in its entirety, there are more than 16 million people with Age Associated Memory Impairment in the U.S. alone.

An advisory panel to the US Food and Drug Administration ruled on Mar. 13, 2001, that MCI, "a condition separate from dementia in Alzheimer's Disease (AD)," is a valid target for new drug therapies, regardless of whether a particular drug also slows the progression to dementia.

However, so far the drugs that are being used in the treatment of this disease only have mild, temporary effects. Therefore cognitive impairment is still an area of high unmet medical need with no effective drugs. The moderate and inconsistent effect observed with some drugs, e.g. cholinesterase inhibitors, indicates that more effective and safe treatments are needed.

SUMMARY OF THE INVENTION

Accordingly, it is one object of the present invention to provide novel methods for preventing and/or treating Cognitive Impairment.

It is another object of the present invention to provide novel methods for preventing and/or treating Mild Cognitive Impairment.

It is another object of the present invention to provide novel methods for preventing and/or reducing the risk of developing Alzheimer's Disease in a cognitively normal subject.

These and other objects, which will become apparent during the following detailed description, have been achieved by the inventors' discovery that certain 1-phenyl-alkanecarboxylic acid compounds may be used for preventing and/or treating Cognitive Impairment, for preventing and/or treating Mild Cognitive Impairment, and for preventing and/or reducing the risk of developing Alzheimer's Disease in a cognitively normal subject.

Thus, the present invention provides:

(1) A method for the treatment and/or prevention of mild cognitive impairment comprising administering, to a subject in need thereof, an effective amount of a compound of formula (I):

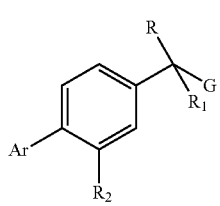

wherein:

R and $R_1$ are the same and are selected from the group of linear or branched $C_1$-$C_4$ alkyl; otherwise they form a 3 to 6 carbon atoms ring with the carbon atom to which they are linked;

G is: a COOR" group wherein R" is H, linear or branched $C_1$-$C_4$ alkyl, $C_3$-$C_6$ cycloalkyl or ascorbyl; a $CONH_2$ or a $CONHSO_2R'''$ group wherein R''' is linear or branched $C_1$-$C_4$ alkyl or $C_3$-$C_6$ cycloalkyl; a tetrazolyl residue;

$R_2$ is H, $CF_3$, $OCF_3$ or a halogen selected from the group of F, Cl, Br, I, preferably fluorine. Ar is a group of formula

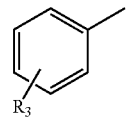

wherein $R_3$ represents one or more groups independently selected from:

halogen as previously defined;

—$CF_3$;

$C_3$-$C_8$ cycloalkyl optionally substituted with one or more $C_1$-$C_4$ alkyl and/or oxo groups;

—CH=$CH_2$;

—CN;

—$CH_2OH$;

methylendioxy or ethylendioxy;

—$NO_2$;

phenyl optionally substituted with one or more of the following groups:

halogen;

—$CF_3$;

—$OCF_3$;

—OH;

linear or branched $C_1$-$C_4$ alkyl;

a saturated heterocycle with at least 4 carbon atoms and at least 1 heteroatom;

$C_3$-$C_8$ cycloalkyl in turn optionally substituted with one or more of the following groups linear or branched $C_1$-$C_4$ alkyl, $CF_3$ or OH;

—$OR_4$ or —$NHCOR_4$ wherein $R_4$ is $CF_3$, linear or branched $C_2$-$C_6$ alkenyl or alkynyl; benzyl; phenyl optionally substituted with one or more of the following groups: halogen, $CF_3$, $OCF_3$, OH, linear or branched $C_1$-$C_4$ alkyl; a saturated heterocycle with at least 4 carbon atoms and at least 1 heteroatom; $C_3$-$C_8$ cycloalkyl in turn optionally substituted with one or more of the following groups: linear or branched $C_1$-C4 alkyl, $CF_3$ or OH;

$SR_5$, $SO_2R_5$ or $COR_5$ wherein $R_5$ is linear or branched $C_1$-$C_6$ alkyl; otherwise Ar is an eterocycle ring selected from the group of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphthyridine, 1,3-dioxole, 1,3-benzodioxole, optionally substituted with one or more groups R.sub.3 as defined above; pharmaceutically acceptable salts and esters thereof.

(2) A method for the treatment and/or prevention of mild cognitive impairment comprising administering, to a subject in need thereof, an effective amount of a compound of formula (I):

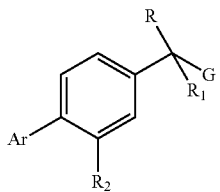

wherein:
R and R₁ are the same and are a linear or a branched $C_1$-$C_4$ alkyl;
G is:
  a —COOR" group wherein R" is H, a linear or a branched $C_1$-$C_4$ alkyl, a
  $C_3$-$C_6$ cycloalkyl, or an ascorbyl;
  a —CONH₂ or a —CONHSO₂R''' group wherein R''' is a linear or a branched $C_1$-$C_4$ alkyl or a $C_3$-$C_6$ cycloalkyl; or
  a tetrazolyl residue;
R₂ is H, $CF_3$, $OCF_3$ or a halogen selected from the group consisting of F, Cl, Br, and I;
Ar is a group of formula

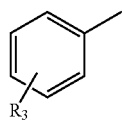

wherein R₃ represents one or more groups independently selected from:
  a halogen selected from the group consisting of F, Cl, Br, and I;
  —$CF_3$;
  —$C_3$-$C_8$ cycloalkyl optionally substituted with one or more $C_1$-$C_4$ alkyl groups, oxo groups, or a combination thereof;
  —CH=CH₂;
  —CN;
  —CH₂OH;
  methylendioxy or ethylendioxy;
  NO₂
  phenyl optionally substituted with one or more of the following groups:
    halogen;
    —$CF_3$;
    —$OCF_3$;
    —OH;
    a linear or a branched $C_1$-$C_4$ alkyl;
    a saturated heterocycle with at least 4 carbon atoms and at least 1 heteroatom;
    a $C_3$-$C_8$ cycloalkyl in turn optionally substituted with one or more of the following groups: a linear or a branched $C_1$-$C_4$ alkyl, —$CF_3$ or —OH;
  —OR₄ or —NHCOR₄ wherein R₄ is —$CF_3$, a linear or a branched $C_2$-$C_6$ alkenyl or alkynyl; a benzyl; a phenyl optionally substituted with one or more of the following groups: halogen, —$CF_3$, —$OCF_3$, —OH, a linear or a branched $C_1$-$C_4$ alkyl; a saturated heterocycle with at least 4 carbon atoms and at least 1 heteroatom; a $C_3$-$C_8$ cycloalkyl in turn optionally substituted with one or more of the following groups: a linear or a branched $C_1$-$C_4$ alkyl, —$CF_3$ or —OH; —SR₅, —SO₂R₅ or —COR₅ wherein R₅ is a linear or a branched $C_1$-$C_6$ alkyl; otherwise Ar is a substituted or unsubstituted heterocyclic ring selected from the group consisting of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphtiridine, 1,3-dioxole, and 1,3-benzodioxole, each of which may be substituted with one or more R₃ groups;
or a pharmaceutically acceptable salt or ester thereof;
with the condition that when R and R₁ are CH₃, R₂ is fluorine.

(3) A method according to (1), wherein R₂ is fluorine.
(4) A method according to (1), wherein R₂ is fluorine; G is a —COOR" group in which R" is H, a linear or a branched $C_1$-$C_4$ alkyl, a $C_3$-$C_6$ cycloalkyl or ascorbyl.
(5) A method according to (1), wherein R₂ is fluorine; G is a —CONH₂ or —CONHSO₂R''' in which R''' is a linear or a branched $C_1$-$C_4$ alkyl or a $C_3$-$C_6$ cycloalkyl.
(6) A method according to (1), wherein both R and R₁ are CH₃; R₂ is fluorine; G is —COOR" in which R" is H, a linear or a branched $C_1$-$C_4$ alkyl, a $C_3$-$C_6$ cycloalkyl, or ascorbyl.
(7) A method according to (1), wherein both R and R₁ are CH₃; R₂ is fluorine; G is a —CONH₂ or —CONHSO₂R" in which R''' is a linear or a branched $C_1$-$C_4$ alkyl or a $C_3$-$C_6$ cycloalkyl; and Ar is phenyl substituted with an optionally substituted phenyl.
(8) A method according to (1), wherein R₂ is fluorine; G is a —COOR" group in which R" is H, a linear or a branched $C_1$-$C_4$ alkyl, a $C_3$-$C_6$ cycloalkyl, or ascorbyl; Ar is a substituted or unsubstituted heterocyclic ring selected from the group consisting of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphtiridine, 1,3-dioxole, and 1,3-benzodioxole.
(9) A method according to (1), wherein both R and R₁ are CH₃; G is a —COOR" group in which R" is H, a linear or a branched $C_1$-$C_4$ alkyl or a $C_3$-$C_6$ cycloalkyl, or an ascorbyl R₂ is fluorine; and Ar is a substituted or unsubstituted heterocyclic ring selected from the group consisting of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphtiridine, 1,3-dioxole, and 1,3-benzodioxole.
(10) A method for the treatment and/or prevention of mild cognitive impairment, comprising administering, to a subject in need thereof, an effective amount of a compound of formula (I):

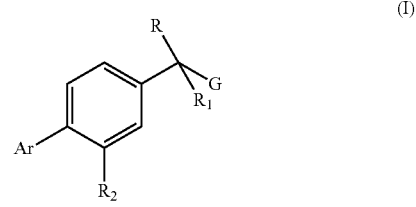

wherein:
R and R₁ are both methyl;
G is:
a —COOR'' group wherein R'' is H or a linear or a branched $C_1$-$C_4$ alkyl group; or
a —CONH₂ or a —CONHSO₂R''' group wherein R''' is a linear or a branched $C_1$-$C_4$ alkyl or a $C_3$-$C_6$ cycloalkyl group;
R₂ is F;
Ar is a group of formula

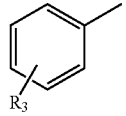

wherein R₃ represents one or more groups independently selected from:
—CF₃;
—$C_3$-$C_8$ cycloalkyl;
phenyl optionally substituted with one or more of the following groups:
halogen;
—CF₃;
—OCF₃;
—OH;
a linear or a branched $C_1$-$C_4$ alkyl;
a saturated heterocycle with at least 4 carbon atoms and at least 1 heteroatom;
a $C_3$-$C_8$ cycloalkyl in turn optionally substituted with one or more of the following groups: a linear or a branched $C_1$-$C_4$ alkyl, —CF₃ or —OH;
—OR₄ or —NHCOR₄ wherein R₄ is —CF₃, a linear or a branched $C_2$-$C_6$ alkenyl or alkynyl; a benzyl; a phenyl optionally substituted with one or more of the following groups: halogen, —CF₃, —OCF₃, —OH, a linear or a branched $C_1$-$C_4$ alkyl; a saturated heterocycle with at least 4 carbon atoms and at least 1 heteroatom; a $C_3$-$C_8$ cycloalkyl in turn optionally substituted with one or more of the following groups: a linear or a branched $C_1$-$C_4$ alkyl, —CF₃ or —OH;
—SR₅, —SO₂R₅ or —COR₅ wherein R₅ is a linear or a branched $C_1$-$C_6$ alkyl;
or a pharmaceutically acceptable salt or ester thereof.

(11) A method according to (9), wherein G is a —COOR'' group in which R'' is H or a linear or a branched $C_1$-$C_4$ alkyl group.

(12) A method for the treatment and/or prevention of mild cognitive impairment, comprising administering, to a subject in need thereof, an effective amount of compound of formula (I):

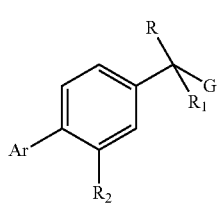

(I)

wherein:
R and R₁ are the same and are a linear or a branched $C_1$-$C_4$ alkyl;
G is a —CONH₂ or a —CONHSO₂R''' group wherein R''' is a linear or a branched $C_1$-$C_4$ alkyl or a $C_3$-$C_6$ cycloalkyl;
R₂ is F;
Ar is a group of formula

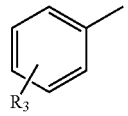

wherein R₃ represents one or more groups independently selected from:
a halogen selected from the group consisting of F, Cl, Br, and I;
—CF₃;
—$C_3$-$C_8$ cycloalkyl optionally substituted with one or more $C_1$-$C_4$ alkyl groups, oxo groups, or a combination thereof;
—CH=CH₂;
—CN;
—CH₂OH;
methylendioxy or ethylendioxy;
NO₂
phenyl optionally substituted with one or more of the following groups:
halogen;
—CF₃;
—OCF₃;
—OH;
a linear or a branched $C_1$-$C_4$ alkyl;
a saturated heterocycle with at least 4 carbon atoms and at least 1 heteroatom;
a $C_3$-$C_8$ cycloalkyl in turn optionally substituted with one or more of the following groups: a linear or a branched $C_1$-$C_4$ alkyl, —CF₃ or —OH; —OR₄ or —NHCOR₄ wherein R₄ is —CF₃, a linear or a branched $C_2$-$C_6$ alkenyl or alkynyl; a benzyl; a phenyl optionally substituted with one or more of the following groups: halogen, —CF₃, —OCF₃, —OH, a linear or a branched $C_1$-$C_4$ alkyl; a saturated heterocycle with at least 4 carbon atoms and at least 1 heteroatom; a $C_3$-$C_8$ cycloalkyl in turn optionally substituted with one or more of the following groups: a linear or a branched $C_1$-$C_4$ alkyl, —CF₃ or —OH; —SR₅, —SO₂R₅ or —COR₅ wherein R₅ is a linear or a branched $C_1$-$C_6$ alkyl; or Ar is a substituted or unsubstituted heterocyclic ring selected from the group consisting of thiophene, benzothiophene, dibenzothiophene, thianthrene, pyrrole, pyrazole, furan, benzofuran, dibenzofuran, indole, isoindole, benzofuran, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphtiridine, 1,3-dioxole, and 1,3-benzodioxole, each of which may be substituted with one or more R₃ groups;
or a pharmaceutically acceptable salt or ester thereof.

(13) A method for the treatment and/or prevention of mild cognitive impairment, comprising administering, to a subject in need thereof, an effective amount of compound of formula (I):

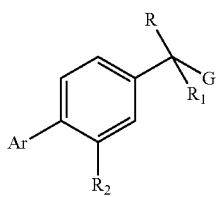

wherein:
R and $R_1$ are both methyl;
G is a —$CONH_2$ or a —$CONHSO_2R'''$ group wherein $R'''$ is a linear or a branched $C_1$-$C_4$ alkyl or a $C_3$-$C_6$ cycloalkyl;
$R_2$ is F; and
Ar is phenyl substituted with an optionally substituted phenyl group,
or a pharmaceutically acceptable salt thereof.

(14) A method for the treatment and/or prevention of mild cognitive impairment, comprising administering, to a subject in need thereof, an effective amount of compound selected from the group consisting of:
2-methyl-2(2-fluoro-4'-trifluoromethylbiphen-4-yl)propionic acid;
a pharmaceutically acceptable salt of 2-methyl-2(2-fluoro-4'-trifluoromethylbiphen-4-yl)propionic acid;
a pharmaceutically acceptable ester of 2-methyl-2(2-fluoro-4'-trifluoromethylbiphen-4-yl)propionic acid;
2-methyl-2(2-fluoro-4'-cyclohexylbiphen-4-yl)propionic acid;
a pharmaceutically acceptable salt of 2-methyl-2(2-fluoro-4'-cyclohexylbiphen-4-yl)propionic acid; and
a pharmaceutically acceptable ester of 2-methyl-2(2-fluoro-4'-cyclohexylbiphen-4-yl)propionic acid.

(15) A method for the treatment and/or prevention of mild cognitive impairment, comprising administering, to a subject in need thereof, an effective amount of 2-methyl-2(2-fluoro-4'-trifluoromethylbiphen-4-yl)propionic acid or a pharmaceutically acceptable salt or ester thereof.

(16) A method for the treatment and/or prevention of mild cognitive impairment, comprising administering, to a subject in need thereof, an effective amount of 2-methyl-2(2-fluoro-4'-cyclohexylbiphen-4-yl)propionic acid or a pharmaceutically acceptable salt or ester thereof.

(17) A method for the treatment and/or prevention of mild cognitive impairment, comprising administering, to a subject in need thereof, an effective amount of a compound or pharmaceutically acceptable salt, which is selected from the group consisting of
1-(2-fluoro-4'-trifluoromethylbiphenyl-4-yl)cyclopropanecarboxylic acid;
1-(3',4'-dichloro-2-fluorobiphenyl-4-yl)cyclopropanecarboxylic acid;
1-[2-fluoro-4'-(4-trifluoromethyl-cyclohexyloxy)-biphenyl-4-yl]-cyclopropanecarboxylic acid;
1-(2,2',4''-trifluoro[1,1';4',1'']terphenyl-4-yl)cyclopropanecarboxylic acid;
1-(2',2''-difluoro-4-hydroxy[1,1';4',1'']terphenyl-4''-yl)cyclopropanecarboxylic acid;
1-(2,2''-difluoro-4''-hydroxy[1,1';4',1'']terphenyl-4-yl)cyclopropanecarboxylic acid; and
pharmaceutically acceptable salts thereof.

(18) A method for the treatment and/or prevention of mild cognitive impairment, comprising administering, to a subject in need thereof, an effective amount of a compound or pharmaceutically acceptable salt, which is selected from the group consisting of
1-(2-fluoro-4'-trifluoromethylbiphenyl-4-yl)cyclopropanecarboxylic acid;
1-(2-fluoro-3'-trifluoromethoxybiphenyl-4-yl)cyclopropanecarboxylic acid;
1-(2-fluoro-4'-trifluoromethoxybiphenyl-4-yl)cyclopropanecarboxylic acid;
1-(2-fluoro-3'-trifluoromethylbiphenyl-4-yl)-cyclopropanecarboxylic acid;
1-[2-fluoro-4'-(tetrahydro-pyran-4-yloxy)-biphenyl-4-yl]-cyclopropanecarboxylic acid;
1-(2,3',4'-trifluorobiphenyl-4-yl)cyclopropanecarboxylic acid;
1-(3',4'-dichloro-2-fluorobiphenyl-4-yl)cyclopropanecarboxylic acid;
1-(3'-chloro-2,4'-difluorobiphenyl-4-yl)cyclopropanecarboxylic acid;
1-[2-fluoro-4'-(4-oxo-cyclohexyl)-biphenyl-4-yl]cyclopropanecarboxylic acid;
2-(2''-fluoro-4-hydroxy-[1,1';  4',1']terphenyl-4''-yl)propionic acid;
1-(2,2',4''-trifluoro[1,1';4',1'']terphenyl-4-yl)cyclopropanecarboxylic acid;
1-(2',2''-difluoro-4-hydroxy[1,1';4',1'']terphenyl-4''-yl)cyclopropanecarboxylic acid;
1-(2,2'-difluoro-4''-hydroxy[1,1';4'',1'']terphenyl-4-yl)cyclopropanecarboxylic acid; and
pharmaceutically acceptable salts thereof.

(19) A method for the treatment and/or prevention of mild cognitive impairment, comprising administering, to a subject in need thereof, an effective amount of 1-(2-fluoro-4'-trifluoromethylbiphenyl-4-yl)cyclopropanecarboxylic acid or a pharmaceutically acceptable salt thereof.

(20) A method for the treatment and/or prevention of mild cognitive impairment, comprising administering, to a subject in need thereof, an effective amount of 1-(3',4'-dichloro-2-fluorobiphenyl-4-yl)cyclopropanecarboxylic acid or a pharmaceutically acceptable salt thereof.

(21) A method for the treatment and/or prevention of mild cognitive impairment, comprising administering, to a subject in need thereof, an effective amount of 1-[2-fluoro-4'-(4-trifluoromethyl-cyclohexyloxy)-biphenyl-4-yl]cyclopropanecarboxylic acid or a pharmaceutically acceptable salt thereof.

(22) A method for the treatment and/or prevention of mild cognitive impairment, comprising administering, to a subject in need thereof, an effective amount of 1-(2,2',4''-trifluoro[1,1';4',1'']terphenyl-4-yl)cyclopropanecarboxylic acid or a pharmaceutically acceptable salt thereof.

(23) A method for the treatment and/or prevention of mild cognitive impairment, comprising administering, to a subject in need thereof, an effective amount of 1-(2',2''-difluoro-4-hydroxy[1,1';4',1'']terphenyl-4''-yl)cyclopropanecarboxylic acid or a pharmaceutically acceptable salt thereof.

(24) A method for the treatment and/or prevention of mild cognitive impairment, comprising administering, to a subject in need thereof, an effective amount of 1-(2,2'-difluoro-4''-hydroxy[1,1';4',1'']terphenyl-4-yl)cyclopropanecarboxylic acid or a pharmaceutically acceptable salt thereof.

(25) A method for preventing and/or reducing the risk of developing Alzheimer's Disease in a cognitively normal subject, comprising administering, to said subject, an effective amount of a compound of formula (I):

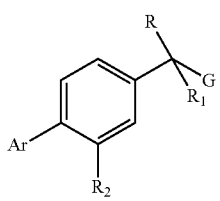

wherein:

R and $R_1$ are the same and are selected from the group of linear or branched $C_1$-$C_4$ alkyl; otherwise they form a 3 to 6 carbon atoms ring with the carbon atom to which they are linked;

G is: a COOR" group wherein R" is H, linear or branched $C_1$-$C_4$ alkyl, $C_3$-$C_6$ cycloalkyl or ascorbyl; a $CONH_2$ or a $CONHSO_2R'''$ group wherein R''' is linear or branched $C_1$-$C_4$ alkyl or $C_3$-$C_6$ cycloalkyl; a tetrazolyl residue;

$R_2$ is H, $CF_3$, $OCF_3$ or a halogen selected from the group of F, Cl, Br, I, preferably fluorine. Ar is a group of formula

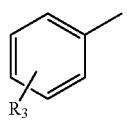

wherein $R_3$ represents one or more groups independently selected from:

halogen as previously defined;
—$CF_3$;
$C_3$-$C_8$ cycloalkyl optionally substituted with one or more $C_1$-$C_4$ alkyl and/or oxo groups;
—CH=$CH_2$;
—CN;
—$CH_2OH$;
methylendioxy or ethylendioxy;
—$NO_2$;
phenyl optionally substituted with one or more of the following groups:
halogen;
—$CF_3$;
—$OCF_3$;
—OH;
linear or branched $C_1$-$C_4$ alkyl;
a saturated heterocycle with at least 4 carbon atoms and at least 1 heteroatom;
$C_3$-$C_8$ cycloalkyl in turn optionally substituted with one or more of the following groups linear or branched $C_1$-$C_4$ alkyl, $CF_3$ or OH;
—$OR_4$ or —$NHCOR_4$ wherein $R_4$ is $CF_3$, linear or branched $C_2$-$C_6$ alkenyl or alkynyl; benzyl; phenyl optionally substituted with one or more of the following groups: halogen, $CF_3$, $OCF_3$, OH, linear or branched $C_1$-$C_4$ alkyl; a saturated heterocycle with at least 4 carbon atoms and at least 1 heteroatom; $C_3$-$C_8$ cycloalkyl in turn optionally substituted with one or more of the following groups: linear or branched $C_1$-C4 alkyl, $CF_3$ or OH;
$SR_5$, $SO_2R_5$ or $COR_5$ wherein $R_5$ is linear or branched $C_1$-$C_6$ alkyl; otherwise Ar is an eterocycle ring selected from the group of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphthyridine, 1,3-dioxole, 1,3-benzodioxole, optionally substituted with one or more groups R.sub.3 as defined above; pharmaceutically acceptable salts and esters thereof.

(26) A method for preventing and/or reducing the risk of developing Alzheimer's Disease in a cognitively normal subject, comprising administering, to said subject, an effective amount of a compound of formula (I):

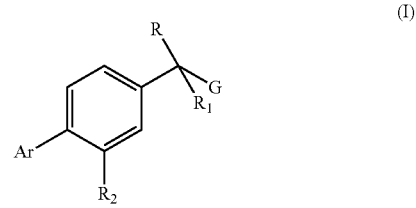

wherein:

R and $R_1$ are the same and are a linear or a branched $C_1$-$C_4$ alkyl;

G is:
a —COOR" group wherein R" is H, a linear or a branched $C_1$-$C_4$ alkyl, a $C_3$-$C_6$ cycloalkyl, or an ascorbyl;
a —$CONH_2$ or a —$CONHSO_2R'''$ group wherein R''' is a linear or a branched $C_1$-$C_4$ alkyl or a $C_3$-$C_6$ cycloalkyl; or
a tetrazolyl residue;

$R_2$ is H, $CF_3$, $OCF_3$ or a halogen selected from the group consisting of F, Cl, Br, and I;

Ar is a group of formula

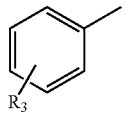

wherein $R_3$ represents one or more groups independently selected from:
a halogen selected from the group consisting of F, Cl, Br, and I;
—$CF_3$;
—$C_3$-$C_8$ cycloalkyl optionally substituted with one or more $C_1$-$C_4$ alkyl groups, oxo groups, or a combination thereof;
—CH=$CH_2$;
—CN;
—$CH_2OH$;
methylendioxy or ethylendioxy;
$NO_2$
phenyl optionally substituted with one or more of the following groups:
halogen;
—$CF_3$;
—$OCF_3$;
—OH;
a linear or a branched $C_1$-$C_4$ alkyl;
a saturated heterocycle with at least 4 carbon atoms and at least 1 heteroatom;
a $C_3$-$C_8$ cycloalkyl in turn optionally substituted with one or more of the following groups: a linear or a branched $C_1$-$C_4$ alkyl, —$CF_3$ or —OH;

—OR$_4$ or —NHCOR$_4$ wherein R$_4$ is —CF$_3$, a linear or a branched C$_2$-C$_6$ alkenyl or alkynyl; a benzyl; a phenyl optionally substituted with one or more of the following groups: halogen, —CF$_3$, —OCF$_3$, —OH, a linear or a branched C$_1$-C$_4$ alkyl; a saturated heterocycle with at least 4 carbon atoms and at least 1 heteroatom; a C$_3$-C$_8$ cycloalkyl in turn optionally substituted with one or more of the following groups: a linear or a branched C$_1$-C$_4$ alkyl, —CF$_3$ or —OH;

—SR$_5$, —SO$_2$R$_5$ or —COR$_5$ wherein R$_5$ is a linear or a branched C$_1$-C$_6$ alkyl; otherwise Ar is a substituted or unsubstituted heterocyclic ring selected from the group consisting of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphtiridine, 1,3-dioxole, and 1,3-benzodioxole, each of which may be substituted with one or more R$_3$ groups;

or a pharmaceutically acceptable salt or ester thereof;
with the condition that when R and R$_1$ are CH$_3$, R$_2$ is fluorine.

(27) A method according to (25), wherein R$_2$ is fluorine.

(28) A method according to (25), wherein R$_2$ is fluorine; G is a —COOR" group in which R" is H, a linear or a branched C$_1$-C$_4$ alkyl, a C$_3$-C$_6$ cycloalkyl or ascorbyl.

(29) A method according to (25), wherein R$_2$ is fluorine; G is a —CONH$_2$ or —CONHSO$_2$R''' in which R''' is a linear or a branched C$_1$-C$_4$ alkyl or a C$_3$-C$_6$ cycloalkyl.

(30) A method according to (25), wherein both R and R$_1$ are CH$_3$; R$_2$ is fluorine; G is —COOR" in which R" is H, a linear or a branched C$_1$-C$_4$ alkyl, a C$_3$-C$_6$ cycloalkyl, or ascorbyl.

(31) A method according to (25), wherein both R and R$_1$ are CH$_3$; R$_2$ is fluorine; G is a —CONH$_2$ or —CONHSO$_2$R''' in which R''' is a linear or a branched C$_1$-C$_4$ alkyl or a C$_3$-C$_6$ cycloalkyl; and Ar is phenyl substituted with an optionally substituted phenyl.

(32) A method according to (25), wherein R$_2$ is fluorine; G is a —COOR" group in which R" is H, a linear or a branched C$_1$-C$_4$ alkyl, a C$_3$-C$_6$ cycloalkyl, or ascorbyl; Ar is a substituted or unsubstituted heterocyclic ring selected from the group consisting of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphtiridine, 1,3-dioxole, and 1,3-benzodioxole.

(33) A method according to (25), wherein both R and R$_1$ are CH$_3$; G is a —COOR" group in which R" is H, a linear or a branched C$_1$-C$_4$ alkyl or a C$_3$-C$_6$ cycloalkyl, or an ascorbyl R$_2$ is fluorine; and Ar is a substituted or unsubstituted heterocyclic ring selected from the group consisting of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphtiridine, 1,3-dioxole, and 1,3-benzodioxole.

(34) A method for preventing and/or reducing the risk of developing Alzheimer's Disease in a cognitively normal subject, comprising administering, to said subject, an effective amount of a compound of formula (I):

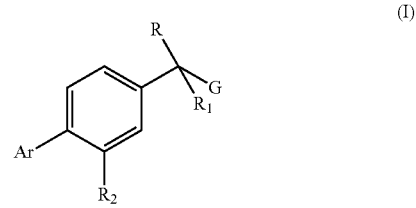

wherein:
R and R$_1$ are both methyl;
G is:
a —COOR" group wherein R" is H or a linear or a branched C$_1$-C$_4$ alkyl group; or
a —CONH$_2$ or a —CONHSO$_2$R''' group wherein R''' is a linear or a branched C$_1$-C$_4$ alkyl or a C$_3$-C$_6$ cycloalkyl group;
R$_2$ is F;
Ar is a group of formula

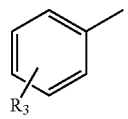

wherein R$_3$ represents one or more groups independently selected from:
—CF$_3$;
—C$_3$-C$_8$ cycloalkyl;
phenyl optionally substituted with one or more of the following groups:
halogen;
—CF$_3$;
—OCF$_3$;
—OH;
a linear or a branched C$_1$-C$_4$ alkyl;
a saturated heterocycle with at least 4 carbon atoms and at least 1 heteroatom;
a C$_3$-C$_8$ cycloalkyl in turn optionally substituted with one or more of the following groups: a linear or a branched C$_1$-C$_4$ alkyl, —CF$_3$ or —OH;
—OR$_4$ or —NHCOR$_4$ wherein R$_4$ is —CF$_3$, a linear or a branched C$_2$-C$_6$ alkenyl or alkynyl; a benzyl; a phenyl optionally substituted with one or more of the following groups: halogen, —CF$_3$, —OCF$_3$, —OH, a linear or a branched C$_1$-C$_4$ alkyl; a saturated heterocycle with at least 4 carbon atoms and at least 1 heteroatom; a C$_3$-C$_8$ cycloalkyl in turn optionally substituted with one or more of the following groups: a linear or a branched C$_1$-C$_4$ alkyl, —CF$_3$ or —OH;
—SR$_5$, —SO$_2$R$_5$ or —COR$_5$ wherein R$_5$ is a linear or a branched C$_1$-C$_6$ alkyl; or a pharmaceutically acceptable salt or ester thereof.

(35) A method according to (34), wherein G is a —COOR" group in which R" is H or a linear or a branched C$_1$-C$_4$ alkyl group.

(36) A method for preventing and/or reducing the risk of developing Alzheimer's Disease in a cognitively normal subject, comprising administering, to said subject, an effective amount of compound of formula (I):

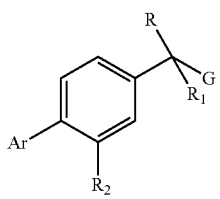

wherein:
R and $R_1$ are the same and are a linear or a branched $C_1$-$C_4$ alkyl;
G is a —$CONH_2$ or a —$CONHSO_2R'''$ group wherein $R'''$ is a linear or a branched $C_1$-$C_4$ alkyl or a $C_3$-$C_6$ cycloalkyl;
$R_2$ is F;
Ar is a group of formula

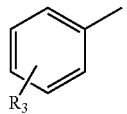

wherein $R_3$ represents one or more groups independently selected from:
a halogen selected from the group consisting of F, Cl, Br, and I;
—$CF_3$;
—$C_3$-$C_8$ cycloalkyl optionally substituted with one or more $C_1$-$C_4$ alkyl groups, oxo groups, or a combination thereof;
—CH=$CH_2$;
—CN;
—$CH_2OH$;
methylendioxy or ethylendioxy;
$NO_2$
phenyl optionally substituted with one or more of the following groups:
halogen;
—$CF_3$;
—$OCF_3$;
—OH;
a linear or a branched $C_1$-$C_4$ alkyl;
a saturated heterocycle with at least 4 carbon atoms and at least 1 heteroatom;
a $C_3$-$C_8$ cycloalkyl in turn optionally substituted with one or more of the following groups: a linear or a branched $C_1$-$C_4$ alkyl, —$CF_3$ or —OH;
—$OR_4$ or —$NHCOR_4$ wherein $R_4$ is —$CF_3$, a linear or a branched $C_2$-$C_6$ alkenyl or alkynyl; a benzyl; a phenyl optionally substituted with one or more of the following groups: halogen, —$CF_3$, —$OCF_3$, —OH, a linear or a branched $C_1$-$C_4$ alkyl; a saturated heterocycle with at least 4 carbon atoms and at least 1 heteroatom; a $C_3$-$C_8$ cycloalkyl in turn optionally substituted with one or more of the following groups: a linear or a branched $C_1$-$C_4$ alkyl, —$CF_3$ or —OH; —$SR_5$, —$SO_2R_5$ or —$COR_5$ wherein $R_5$ is a linear or a branched $C_1$-$C_6$ alkyl; or Ar is a substituted or unsubstituted heterocyclic ring selected from the group consisting of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphtiridine, 1,3-dioxole, and 1,3-benzodioxole, each of which may be substituted with one or more $R_3$ groups;
or a pharmaceutically acceptable salt or ester thereof.

(37) A method for preventing and/or reducing the risk of developing Alzheimer's Disease in a cognitively normal subject, comprising administering, to said subject, an effective amount of compound of formula (I):

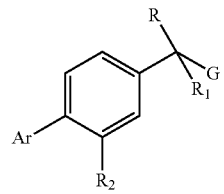

wherein:
R and $R_1$ are both methyl;
G is a —$CONH_2$ or a —$CONHSO_2R'''$ group wherein $R'''$ is a linear or a branched $C_1$-$C_4$ alkyl or a $C_3$-$C_6$ cycloalkyl;
$R_2$ is F; and
Ar is phenyl substituted with an optionally substituted phenyl group,
or a pharmaceutically acceptable salt thereof.

(38) A method for preventing and/or reducing the risk of developing Alzheimer's Disease in a cognitively normal subject, comprising administering, to said subject, an effective amount of compound selected from the group consisting of:
2-methyl-2(2-fluoro-4'-trifluoromethylbiphen-4-yl)propionic acid;
a pharmaceutically acceptable salt of 2-methyl-2(2-fluoro-4'-trifluoromethylbiphen-4-yl)propionic acid;
a pharmaceutically acceptable ester of 2-methyl-2(2-fluoro-4'-trifluoromethylbiphen-4-yl)propionic acid;
2-methyl-2(2-fluoro-4'-cyclohexylbiphen-4-yl)propionic acid;
a pharmaceutically acceptable salt of 2-methyl-2(2-fluoro-4'-cyclohexylbiphen-4-yl)propionic acid; and
a pharmaceutically acceptable ester of 2-methyl-2(2-fluoro-4'-cyclohexylbiphen-4-yl)propionic acid.

(39) A method for preventing and/or reducing the risk of developing Alzheimer's Disease in a cognitively normal subject, comprising administering, to said subject, an effective amount of 2-methyl-2(2-fluoro-4'-trifluoromethylbiphen-4-yl)propionic acid or a pharmaceutically acceptable salt or ester thereof.

(40) A method for preventing and/or reducing the risk of developing Alzheimer's Disease in a cognitively normal subject, comprising administering, to said subject, an effective amount of 2-methyl-2(2-fluoro-4'-cyclohexylbiphen-4-yl)propionic acid or a pharmaceutically acceptable salt or ester thereof.

(41) A method for preventing and/or reducing the risk of developing Alzheimer's Disease in a cognitively normal subject, comprising administering, to said subject, an effective amount of a compound or pharmaceutically acceptable salt, which is selected from the group consisting of
1-(2-fluoro-4'-trifluoromethylbiphenyl-4-yl)cyclopropanecarboxylic acid;
1-(3',4'-dichloro-2-fluorobiphenyl-4-yl)cyclopropanecarboxylic acid;

1-[2-fluoro-4'-(4-trifluoromethyl-cyclohexyloxy)-biphenyl-4-yl]-cyclopropanecarboxylic acid;
1-(2,2',4"-trifluoro[1,1';4',1"]terphenyl-4-yl)cyclopropanecarboxylic acid;
1-(2',2"-difluoro-4-hydroxy[1,1';4',1"]terphenyl-4"-yl)cyclopropanecarboxylic acid;
1-(2,2"-difluoro-4"-hydroxy[1,1';4',1"]terphenyl-4-yl)cyclopropanecarboxylic acid; and
pharmaceutically acceptable salts thereof.

(42) A method for preventing and/or reducing the risk of developing Alzheimer's Disease in a cognitively normal subject, comprising administering, to said subject, an effective amount of a compound or pharmaceutically acceptable salt, which is selected from the group consisting of
1-(2-fluoro-4'-trifluoromethylbiphenyl-4-yl)cyclopropanecarboxylic acid;
1-(2-fluoro-3'-trifluoromethoxybiphenyl-4-yl)cyclopropanecarboxylic acid;
1-(2-fluoro-4'-trifluoromethoxybiphenyl-4-yecyclopropanecarboxylic acid;
1-(2-fluoro-3'-trifluoromethylbiphenyl-4-yl)-cyclopropanecarboxylic acid;
1-[2-fluoro-4'-(tetrahydro-pyran-4-yloxy)-biphenyl-4-yl]-cyclopropanecarboxylic acid;
1-(2,3',4'-trifluorobiphenyl-4-yl)cyclopropanecarboxylic acid;
1-(3',4'-dichloro-2-fluorobiphenyl-4-yl)cyclopropanecarboxylic acid;
1-(3'-chloro-2,4'-difluorobiphenyl-4-yl)cyclopropanecarboxylic acid;
1-[2-fluoro-4'-(4-oxo-cyclohexyl)-biphenyl-4-yl]cyclopropanecarboxylic acid;
2-(2"-fluoro-4-hydroxy-[1,1';4',1"]terphenyl-4"-yl)propionic acid;
1-(2,2',4"-trifluoro[1,1';4',1"]terphenyl-4-yl)cyclopropanecarboxylic acid;
1-(2,2"-difluoro-4-hydroxy[1,1';4',1"]terphenyl-4"-yl)cyclopropanecarboxylic acid;
1-(2,2'-difluoro-4"-hydroxy[1,1';4",1"]terphenyl-4-yl)cyclopropanecarboxylic acid; and
pharmaceutically acceptable salts thereof.

(43) A method for preventing and/or reducing the risk of developing Alzheimer's Disease in a cognitively normal subject, comprising administering, to said subject, an effective amount of 1-(2-fluoro-4'-trifluoromethylbiphenyl-4-yl)cyclopropanecarboxylic acid or a pharmaceutically acceptable salt thereof.

(44) A method for preventing and/or reducing the risk of developing Alzheimer's Disease in a cognitively normal subject, comprising administering, to said subject, an effective amount of 1-(3',4'-dichloro-2-fluorobiphenyl-4-yl)cyclopropanecarboxylic acid or a pharmaceutically acceptable salt thereof.

(45) A method for preventing and/or reducing the risk of developing Alzheimer's Disease in a cognitively normal subject, comprising administering, to said subject, an effective amount of 1-[2-fluoro-4'-(4-trifluoromethyl-cyclohexyloxy)-biphenyl-4-yl]cyclopropanecarboxylic acid or a pharmaceutically acceptable salt thereof.

(46) A method for preventing and/or reducing the risk of developing Alzheimer's Disease in a cognitively normal subject, comprising administering, to said subject, an effective amount of 1-(2,2',4"-trifluoro[1,1';4',1"]terphenyl-4-yl)cyclopropanecarboxylic acid or a pharmaceutically acceptable salt thereof.

(47) A method for preventing and/or reducing the risk of developing Alzheimer's Disease in a cognitively normal subject, comprising administering, to said subject, an effective amount of 1-(2',2"-difluoro-4-hydroxy[1,1';4',1"]terphenyl-4"-yl)cyclopropanecarboxylic acid or a pharmaceutically acceptable salt thereof.

(48) A method for preventing and/or reducing the risk of developing Alzheimer's Disease in a cognitively normal subject, comprising administering, to said subject, an effective amount of 1-(2,2'-difluoro-4"-hydroxy[1,1';4',1"]terphenyl-4-yl)cyclopropanecarboxylic acid or a pharmaceutically acceptable salt thereof.

DETAILED DESCRIPTION OF THE PREFERRED EMBODIMENTS

Unless defined otherwise, all technical and scientific terms used herein have the same meaning as it is commonly understood by one of skill in the art to which this subject matter belongs.

All the terms "active drug," "active ingredient," "active," "active substance," "active compound," and "therapeutic agent" are used synonymously.

As used herein, "an effective amount of a compound for treating a particular disease" is an amount that is sufficient to ameliorate, or in some manner reduce, the symptoms associated with the disease.

As used herein, the term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

As used herein the terms "prevention" and "preventing" mean reducing the occurrence of the disease, reducing the likelihood of contracting the disease, or delaying the onset of the disease.

As used herein, the term "improving cognitive function" includes "promoting" cognitive function (affecting impaired cognitive function in the subject so that it more closely resembles the function of an aged-matched normal, unimpaired subject, including affecting states in which cognitive function is reduced compared to a normal subject) and "preserving" cognitive function (affecting normal or impaired cognitive function such that it does not decline or does not fall below that observed in the subject upon first presentation or diagnosis, e.g., to the extent of expected decline in the absence of treatment).

With the term "APOE", it is meant a class of apolipoproteins essential for the normal catabolism of triglyceride-rich lipoprotein constituents. ApoE is polymorphic with three major isoforms ApoE2, ApoE3, ApoE4. The form E4 has been implicated in impaired cognitive function.

By "subject suffering from Mild Cognitive Impairment," it is meant a subject which meets the criteria for MCI as desribed in Petersen R C, et al., *J. Intern. Med.,* 256: 183-194 (2004); Petersen R C, et al., *Arch. Neurol.,* 56: 303-308 (1999); and Petersen R C, et al., *Arch. Neurol.,* 66: 1447-1455 (2009), all of which are incorporated herein by reference in their entireties):

1) Memory complaint, preferably corroborated by an informant;
2) Memory impairment documented according to appropriate reference values;

3) Essentially normal performance in non-memory cognitive domains;
4) Generally preserved activities of daily living;
5) Not demented.

In the case of non-amnestic MCI patients, criterium 2 of the original Petersen et al's criteria (see Petersen R C, et al., *Arch. Neurol.*, 56: 303-308 (1999), which is incorporated herein by reference in its entirety) is also integrated with the diagnostic decision process suggested by Petersen (see Petersen R C, et al., *J. Intern. Med.*, 256: 183-194 (2004), which is incorporated herein by reference in its entirety).

By "cognitively normal subject," it is meant a subject that does not suffer from Mild Cognitive Impairment, Dementia, or Alzheimer's Disease.

Thus, in a first embodiment, the present invention provides a method for preventing and/or treating Cognitive Impairment, by administering, to a subject in need thereof, an effective amount of certain 1-phenylalkanecarboxylic acid compounds or a pharmaceutically acceptable salt thereof.

In a second embodiment, the present invention provides a method for preventing and/or treating Mild Cognitive Impairment, by administering, to a subject in need thereof, an effective amount of certain 1-phenylalkanecarboxylic acid compounds or a pharmaceutically acceptable salt thereof.

In another embodiment, the present invention provides a method for preventing and/or reducing the risk of developing Alzheimer's Disease in a cognitively normal subject, by administering, to a subject, an effective amount of certain 1-phenylalkanecarboxylic acid compounds or a pharmaceutically acceptable salt thereof.

With reference to formula (I), a first group of preferred compounds is that in which: R and $R_1$ form a 3 carbon atoms ring with the carbon atom to which they are linked;
$R_2$ is fluorine;
G is COOR", wherein R" is H, linear or branched $C_1$-$C_4$ alkyl, $C_3$-$C_6$ cycloalkyl or ascorbyl;
Ar is phenyl as defined above.

A second group of preferred compounds is that in which:
R and $R_1$ form a 3 carbon atoms ring with the carbon atom to which they are linked;
$R_2$ is fluorine;
G is $CONH_2$ or $CONHSO_2R'''$ wherein R''' is linear or branched $C_1$-$C_4$ alkyl or $C_3$-$C_6$ cycloalkyl;
Ar is phenyl as defined above.

A third group of preferred compounds is that in which:
both R and $R_1$ are methyl;
$R_2$ is fluorine;
G is COOR" wherein R" is as defined above;
Ar is phenyl as defined above.

A fourth group of preferred compounds is that in which:
both R and $R_1$ are methyl;
$R_2$ is fluorine;
G is $CONH_2$ or $CONHSO_2R'''$, wherein R''' is as defined above;
Ar is phenyl as defined above.

A fifth group of preferred compounds is that in which:
R and $R_1$ form a 3 carbon atoms ring with the carbon atom to which they are linked;
$R_2$ is fluorine;
G is COOR" wherein R" is as defined above;
Ar is a heterocycle as defined above.

A sixth group of preferred compounds is that in which:
both R and $R_1$ are methyl;
$R_2$ is fluorine;
G is COOR" wherein R" is as defined above;
Ar is a heterocycle as defined above.

Particularly preferred are the following compounds:
2-methyl-2(2-fluoro-4'-trifluoromethylbiphen-4-yl)propionic acid (CHF 4810);
2-methyl-2(2-fluoro-4'cyclohexyl biphen-4-yl)propionic acid (CHF 4961);
1-(2-fluoro-4'-trifluoromethylbiphenyl-4-yl)cyclopropanecarboxylic acid (CHF 5022);
1-(4'-cyclohexyl-2-fluorobiphenyl-4-yl)cyclopropanecarboxylic acid (CHF 5023);
1-(4'-benzyloxy-2-fluorobiphenyl-4-yl)cyclopropanecarboxylic acid (CHF 5042);
1-(2-fluoro-4'-isopropyloxybiphenyl-4-yl)cyclopropanecarboxylic acid (CHF 5044);
1-(2-fluoro-3'-trifluoromethoxybiphenyl-4-yl)cyclopropanecarboxylic acid (CHF 5045);
1-(2-fluoro-4'-trifluoromethoxybiphenyl-4-yl)cyclopropanecarboxylic acid (CHF 5046);
1-(2-fluoro-3'-trifluoromethylbiphenyl-4-yl)cyclopropanecarboxylic acid (CHF 5058);
1-(4'-cyclopentyl-2-fluorobiphenyl-4-yl)cyclopropanecarboxylic acid (CHF 5059);
1-(4'-cycloheptyl-2-fluorobiphenyl-4-yl)cyclopropanecarboxylic acid (CHF 5060);
1-(2'-cyclohexyl-2-fluorobiphenyl-4-yl)cyclopropanecarboxylic acid (CHF 5061);
1-(2-fluoro-4'-hydroxybiphenyl-4-yl)cyclopropanecarboxylic acid (CHF 5070);
1-[2-fluoro-4'-(tetrahydropyran-4-yloxy)biphenyl-4-yl]-cyclopropanecarboxylic acid (CHF 5071);
1-(2,3',4'-trifluorobiphenyl-4-yl)cyclopropanecarboxylic acid (CHF 5073);
1-(3',4'-dichloro-2-fluorobiphenyl-4-yl)cyclopropanecarboxylic acid (CHF 5074);
1-(3',5'-dichloro-2-fluorobiphenyl-4-yl)cyclopropanecarboxylic acid (CHF 5075);
1-(3'-chloro-2,4'-difluorobiphenyl-4-yl)cyclopropanecarboxylic acid (CHF 5076);
1-(4-benzo[b]thiophen-3-yl-3-fluorophenyl)cyclopropanecarboxylic acid (CHF 5077);
1-(2-fluoro-4'-prop-2-inyloxy-biphenyl-4-yl)-cyclopropanecarboxylic acid (CHF 5078);
1-(4'-cyclohexyloxy-2-fluoro-biphenyl-4-yl)-cyclopropanecarboxylic acid (CHF 5079);
1-[2-fluoro-4'-(tetrahydropyran-4-yl)-biphenyl-4-yl]-cyclopropanecarboxylic acid (CHF 5080);
1-[2-fluoro-4'-(4-oxo-cyclohexyl)-biphenyl-4-yl]-cyclopropanecarboxylic acid (CHF 5081);
2-(2"-fluoro-4-hydroxy-[1,1':4',1"]tert-phenyl-4"-yl)-cyclopropanecarboxylic acid (CHF 5083);
1-[4'-(4,4-dimethylcyclohexyl)-2-fluoro[1,1'-biphenyl]-4-yl]-cyclopropane-carboxylic acid (CHF 5084);
1-[2-fluoro-4'-[[[4-(trifluoromethyl)benzoyl]amino][1,1'-biphenyl]-4-yl]-cyclopropanecarboxylic acid (CHF 5094);
1-[2-fluoro-4'-[[4-(trifluoromethyl)cyclohexyl]oxy][1,1'-biphenyl]-4-yl]-cyclopropanecarboxylic acid (CHF 5096);
1-[2-fluoro-4'-[(3,3,5,5-tetramethylcyclohexyl)oxy][1,1'-biphenyl]-4-yl]-cyclopropanecarboxylic acid (CHF 5102);
1-[4'-[(4,4-dimethylcyclohexyl)oxy]-2-fluoro[1,1'-biphenyl]-4-yl]-cyclopropanecarboxylic acid (CHF 5103);
1-(2,3',4"-trifluoro[1,1':4',1"-tert-phenyl]-4-yl)-cyclopropanecarboxylic acid (CHF 5104);
1-(2,2',4"-trifluoro[1,1':4',1"-tert-phenyl]-4-yl)-cyclopropanecarboxylic acid (CHF 5105);
1-(2,3'-difluoro-4"-hydroxy[1,1':4',1"-tert-phenyl]-4-yl)-cyclopropanecarboxylic acid (CHF 5106);

1-(2,2'-difluoro-4''-hydroxy[1,1':4',1''-ter-phenyl]-4-yl)-cyclopropanecarboxylic acid (CHF 5107);

2-(2-fluoro-3',5'-bis(chloro)biphen-4-yl)propionic acid amide (CHF 5125).

A more preferred group of compounds is that in which R and $R_1$ form a 3 carbon atoms ring with the carbon atom to which they are linked; $R_2$ is fluorine; G is COOH; Ar is phenyl substituted with one or more groups in such a way as that the log P (the partition coefficient between n-octanol and water) of the whole molecule is equal or higher than 4.5 as calculated in silico by using the software QikProp® release version 2.1 (Schrodinger Inc).

It has indeed been found that the higher the log P of the molecule, the greater is the inhibition potency of the release of $A\beta_{42}$ peptide and that particularly potent compounds are those whose log P is equal or higher than 4.5, preferably higher than 5.0.

The compounds and pharmaceutically acceptable salts thereof to be administered in the present invention are described and can be prepared as described in U.S. Pat. No. 7,662,995, which is incorporated herein by reference in its entirety.

In one preferred embodiment, the present methods comprise administration of 1-(3',4'-dichloro-2-fluorobiphenyl-4-yl)cyclopropanecarboxylic acid or a pharmaceutically acceptable salt thereof, the compound of formula (Ia), also known with the internal code CHF 5074:

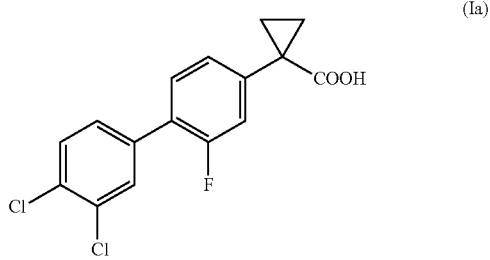 [SMILES: O=C(O)C1(c2ccc(-c3ccc(Cl)c(Cl)c3)c(F)c2)CC1]

(Ia)

In view of the close relationship between the compounds to be administered in the present methods, including the compound of formula (Ia), in the free acid form and those in the form of salts, the present invention is also directed to the use of pharmaceutically acceptable salts thereof. Suitable pharmaceutically acceptable salts according for use in the invention thus include those formed with both common organic and inorganic bases. For example, the salts disclosed in the co-pending patent application WO 2011/120778, which is incorporated herein by reference, may advantageously be utilized.

The compounds and pharmaceutically acceptable salts thereof to be administered in the present methods, including the compound of formula (Ia) and pharmaceutically acceptable salts thereof, may be combined with one or more pharmaceutically acceptable carriers or excipients to provide suitable pharmaceutical compositions. The pharmaceutically acceptable carriers or excipients may be advantageously selected from the group consisting of, diluents, wetting agents, emulsifying agents, binders, coatings, fillers, glidants, lubricants, disintegrants, preservatives, stabilizers, surfactants, pH buffering substances, flavouring agents, and the like. Comprehensive guidance on pharmaceutical excipients is given in *Remington's Pharmaceutical Sciences Handbook*, XVII Ed. Mack Pub., N.Y., U.S.A, which is incorporated herein by reference in its entirety.

The compounds and pharmaceutically acceptable salts thereof to be administered in the present methods, including the compound of formula (Ia) (CHF 5074) and pharmaceutically acceptable salts thereof, may be formulated for administration by any convenient route, e.g. by oral, parenteral, topical, inhalation, buccal, nasal, rectal, and transdermal administration. Suitable dosage forms can include tablets, capsules, lozenges, suppositories, solutions, emulsions, suspensions, syrups, ointments, creams, oils, and powders. Preferably, the pharmaceutical compositions of the present invention will be administered orally using appropriate dosage forms, such as capsules, tablets, caplets etc, more preferably tablets.

In one preferred embodiment, the compounds and pharmaceutically acceptable salts thereof to be administered in the present methods, including the compound of formula (Ia) (CHF 5074) and pharmaceutically acceptable salts thereof, will be administered in the form of tablets, comprising 200 mg of the active ingredient and the following excipients: lactose monohydrate, microcrystalline cellulose, hydroxypropylmethyl cellulose, croscarmellose sodium, sodium lauryl sulphate, and magnesium stearate.

However, it should be recognized that the dosage form may contain other amounts of the compound or pharmaceutically acceptable salt thereof, containing as little as 1 mg, 5 mg, 10 mg, 25 mg, 50 mg, 100 mg, 200 mg, 250 mg, 300 mg, 400 mg, 500 mg, or 1000 mg, and as much as 5 mg, 10 mg, 25 mg, 50 mg, 100 mg, 200 mg, 250 mg, 300 mg, 400 mg, 500 mg, 1000 mg, or 2000 mg, and any amount or range of amounts encompassed by these upper and lower amounts.

In one embodiment, the dosage of the compounds and pharmaceutically acceptable salts thereof to be administered in the present methods, including the compound of formula (Ia) (CHF 5074) and pharmaceutically acceptable salts thereof, and the duration of the treatment can vary within certain limits depending on the type of patient (weight, sex, subject age), the mode of administration and the severity advancement of the pathological condition or the specific memory or cognition disorder treated. A person skilled in the art may determine the optimal therapeutically effective amount and the regimen for each patient and thereby define the appropriate dosage and the duration of the treatment. For example, when the compounds and pharmaceutically acceptable salts thereof to be administered in the present methods, including the compound of formula (Ia) (CHF 5074) and pharmaceutically acceptable salts thereof, are administered by oral route to humans, a typical daily dosage might fall within the range of 100 mg and 800 mg, administered in a single or multiple daily dosage units, preferably between 200 and 600 mg.

In certain embodiments, the daily dose may be of 200 mg, in other embodiments, it may be of 400 mg, in further embodiments of 600 mg.

Of course, the daily dosage may range from as little as 1 mg, 5 mg, 10 mg, 25 mg, 50 mg, 100 mg, 200 mg, 250 mg, 300 mg, 400 mg, 500 mg, or 1000 mg, and as much as 5 mg, 10 mg, 25 mg, 50 mg, 100 mg, 200 mg, 250 mg, 300 mg, 400 mg, 500 mg, 1000 mg, or 2000 mg, and any amount or range of amounts encompassed by these upper and lower amounts.

The duration of the treatment is usually of at least one year, but may be of a lesser or longer duration.

In particular embodiments, the compounds and pharmaceutically acceptable salts thereof to be administered in the present methods, including the compound of formula (Ia) (CHF 5074) and pharmaceutically acceptable salts thereof, may be used in association with other therapeutic agents, for example with anticholinergic agents or with cholinesterase inhibitors and/or acetylcholine modulators.

More in general the present invention provides a safer and highly effective therapeutic method, superior to existing treatments, for treating cognitive disorders.

In fact, the compounds and pharmaceutically acceptable salts thereof to be administered in the present methods, including the compound of formula (Ia) (CHF 5074) and pharmaceutically acceptable salts thereof, are capable of improving Cognitive Function and Treating Cognitive Impairment in a mammal (e.g., human, non human primate or rat).

In one embodiment of the invention, the mammal has normal cognitive function which is improved.

In another embodiment the mammal exhibits cognitive impairment associated with aging.

In another embodiment the mammal is a human with cognitive impairment associated with a disease or disorder.

In another embodiment the mammal is a human exhibiting cognitive function impairment associated with disorders such as autism, dyslexia, attention deficit hyperactivity disorder, schizophrenia, obsessive compulsive disorders, psychosis, bipolar disorders, depression, Tourette's syndrome and disorders of learning in children, adolescents and adults, Age Associated Memory Impairment, Age Associated Cognitive Decline, Parkinson's Disease, Down's Syndrome, traumatic brain injury Huntington's Disease, Progressive Supranuclear Palsy (PSP), HIV, stroke, vascular diseases, Pick's or Creutzfeldt-Jacob diseases, multiple sclerosis (MS), other white matter disorders and drug-induced cognitive worsening.

In another embodiment, the impairment of cognitive function is caused by, or attributed to, Alzheimer's disease.

In a preferred embodiment, the impairment of cognitive function is caused by, or attributed to, mild cognitive impairment (MCI). A population of patients that could particularly benefit of therapeutic method of the invention is that including amnestic MCI APOE4 carriers with parental history of AD, and/or cognitively normal APOE4 carriers with parental history of AD, both of age between 45 and 65 years.

The compounds and pharmaceutically acceptable salts thereof to be administered in the present methods, including the compound of formula (Ia) (CHF 5074) and pharmaceutically acceptable salts thereof, are also capable of preventing and/or reducing the risk of developing AD in cognitively normal subjects.

Preferably, said subjects at the risk of developing Alzheimer's Disease carry the APOE4 gene and have a parental history of AD, more preferably they have an age between 45 and 65 years, two well-known independent risk factors of developing AD (see Debette S et al., *Neurology*, 73: 2071-2078 (2009), which is incorporated herein by reference in its entirety). The protective effects of NSAIDs on the AD onset may be restricted to APOE4 carriers (see Szekely et al., *Neurology*, 70: 17-24 (2008); Yip et al., NBMC Geriatrics, 5: 2 (2005); and Cornelius et al., *Neuroepidemiology*, 23: 135-43 (2004), all of which are incorporated herein by reference in their entireties). It has been shown that NSAIDs use may reduce the risk of AD onset in the middle age but at the same time NSAIDs use can accelerate the onset of AD in cognitively normal subjects with a median age of 75 years (see Breitner et al., *Neurology*, 72: 1899-1905 (2009), which is incorporated herein by reference in its entirety).

Other features of the invention will become apparent in the course of the following descriptions of exemplary embodiments which are given for illustration of the invention and are not intended to be limiting thereof.

EXAMPLES

Example 1

Evaluation of Safety & Tolerability of Multiple Dose Regimens and Determination of Effects on Potential Markers of Clinical Efficacy in Patients with Mild Cognitive Impairment (MCI)

The safety and efficacy of the present methods is determined by selecting a test patient pool, administration of a selected compound or pharmaceutically acceptable salt thereof as described above, and conducting certain assessments as described below.

Inclusion Criteria.

The following criteria are met for inclusion in the evaluation.

Patients must meet all of the following inclusion criteria to be eligible for enrollment into the study:

Patient's written informed consent is obtained prior to any study-related procedures.

Patient is younger than 80 years of age.

Patient has a diagnosis of amnestic or non-amnestic Mild Cognitive Impairment according to modified Petersen, et al's criteria (see Petersen R C, et al., *Arch. Neurol.*, 66: 1447-1455 (2009), which is incorporated herein by reference).

Patient has a Mini-Mental State Examination (MMSE) (see Folstein M F, et al., *J. Psychiatr. Res.*, 12: 189-198 (1975), which is incorporated herein by reference) score higher than 24 at screening.

MRI scan of the brain at screening with fluid-attenuation inversion recovery (FLAIR) and T2*-weighted gradient-recalled-echo (GRE) sequences.

Patient's informant is available.

Exclusion Criteria.

The presence of any of the following will exclude a patient from study enrollment:

A diagnosis of Alzheimer's disease according to the Diagnostic and Statistical Manual of Mental Disorders 4th Edition Text Revision (DSM-IV-TR) (see American Psychiatric Association. Diagnostic and statistical manual of mental disorders, $4^{th}$ edition. Washington, D.C.: American Psychiatric Association, 1994, which is incorporated herein by reference) or National Institute of Neurological and Communicative Disorders and Stroke-AD and Related Disorders (NINCDS-ADRDA) (see McKhann G, et al., *Neurology*, 34: 939-944 (1984), which is incorporated herein by reference) criteria.

Any medical condition that could explain the patient's cognitive deficits (e.g., vitamin B12 or folate deficiency, abnormal thyroid function, posttraumatic conditions, syphilis, multiple sclerosis or another disorder of neuro-inflammation, Parkinson's disease, multi-infarct dementia, Huntington's disease, normal pressure hydrocephalus, CNS tumor, progressive supranuclear palsy, seizure disorder (other than childhood febrile seizures), subdural hematoma).

CT or MRI brain imaging results obtained within 12 months prior to baseline showing evidence of infection, infarction, or focal lesions of clinical significance.

MRI scan at screening showing more than 4 cerebral microhemorrhages (lesions with diameter ≤10 mm), regardless of their anatomical location or diagnostic characterization as "possible" or "definite."

MRI scan at screening showing single area of superficial siderosis, or evidence of a prior macrohemorrhage (lesion with diameter >10 mm).

A Geriatric Depression Scale (30-point scale) (see Yesavage J A, et al., *J. Psychiatr. Res.,* 17: 37-49 (1983), which is incorporated herein by reference) score >9 at screening.

History of stroke. Patients with a history of transient ischemic attack may be enrolled, if it occurred at least three months prior to screening.

A modified Hachinski ischemic scale score >4 at screening.

Women of childbearing potential. Women of childbearing potential include any female who has experienced menarche and who has not undergone successful surgical sterilization (hysterectomy, bilateral tubal ligation, or bilateral oophorectomy) or is not postmenopausal.

Post menopause is defined as:

Amenorrhea ≥12 consecutive months without another cause and a documented serum follicle stimulating hormone (FSH) level >35 mIU/mL (FSH level testing is not required for women ≥62 years old with amenorrhea of ≥1 year).

or

Women with irregular menstrual periods and a documented serum follicle stimulating hormone (FSH) level >35 mIU/mL.

or

Women on hormone replacement therapy.

Women who are using oral contraceptives, other hormonal contraceptives (vaginal products, skin patches, or implanted or injectable products), or mechanical products such as an intrauterine device or barrier methods (diaphragm, condoms, spermicides) to prevent pregnancy, or are practicing abstinence or where their partner is sterile (e.g., vasectomy) should be considered to be of childbearing potential.

Women who are breastfeeding or pregnant.

Women with a positive pregnancy test within 72 hours prior to administration of first dose of study medication.

Sexually active fertile men not using effective birth control if their partners are women of childbearing potential.

Patient has vitamin B12 or folate deficiency. Patients with a B12 deficiency may participate in the study if they are on stable vitamin B12 replacement for at least three months prior to screening.

All skin cancers and any cancer that is being actively treated, as well as cancers that are considered to have a high probability of recurrence (with supporting documentation of this from the treating oncologist, if necessary).

Clinically significant abnormal coagulation tests.

Unstable cardiovascular (includes uncontrolled hypertension), pulmonary, gastrointestinal or hepatic disease one month prior to screening.

Diagnosis of schizophrenia or recurrent mood disorder (including unipolar and bipolar disorders) within 3 years of screening.

Current diagnosis of peptic ulcer or gastrointestinal bleeding within the last year and/or chronic inflammatory bowel disease.

History of neurosyphilis as indicated by positive fluorescent treponemal antibody absorption (FTA-ABS), or microhemagglutination assay (MHA-TP), or treponema pallidum particle agglutination assay (TPPA) tests.

Concomitant use of donepezil at doses >5 mg/day or other cholinesterase inhibitors (rivastigmine or galantamine) at any dose.

Concomitant use of memantine at doses >20 mg/day.

Concomitant use of psychoactive drugs (sedatives, hypnotics, etc.). Stable doses of sedatives for conditions such as mild to moderate anxiety or insomnia may be permitted if they have been stable for at least 30 days prior to randomization. Administration of compound or pharmaceutically acceptable salt.

In the following table, the administration of CHF 5074 is exemplified. It is to be understood, however, the other compounds, salts, and dosages may be used.

The patients are orally treated with tablets comprising 200 mg of CHF 5074 according to the following scheme

| Arms | Assigned Interventions |
| --- | --- |
| CHF 5074 1x: Experimental oral tablet, multidose Intervention: Drug: CHF 5074 1x | Drug: CHF 5074 1x; oral tablet, 1x, once a day in the morning for 12 weeks |
| CHF 5074 2x: Experimental oral tablet, multidose Intervention: Drug: CHF 5074 2x | Drug: CHF 5074 2x; oral tablet, 1x, once a day in the morning for 4 weeks, followed by oral tablet, 2x, once a day in the morning for 8 weeks |
| CHF 5074 3x: Experimental oral tablet, multidose Intervention: Drug: CHF 5074 3x | Drug: CHF 5074 3x; oral tablet, 1x, once a day in the morning for 4 weeks, followed by oral tablet, 2x, once a day in the morning for 4 weeks, followed by oral tablet, 3x, once a day in the morning for 4 weeks |
| Placebo: Placebo Comparator placebo, oral tablet, multidose Intervention: Drug: Placebo | Drug: Placebo oral tablet, once a day in the morning for 12 weeks |

Assessments.

Primary Outcome Measures:

Determine maximum tolerated dose of a compound or pharmaceutically acceptable salt thereof to be administered according to the present invention, including CHF 5074 or a pharmaceutically acceptable salt thereof, after multiple oral once daily administration to patients with mild cognitive impairment (time frame: up to 12 weeks).

Secondary Outcome Measures:

Measurement of trough plasma levels of a compound or pharmaceutically acceptable salt thereof to be administered according to the present invention, including CHF 5074 or a pharmaceutically acceptable salt thereof (time frame: days 29, 57 and 85).

Assessments:

In some of the following descriptions of the assessments and tests that may be performed reference is made to CHF 5074. It is to be understood, however, that these assessments may be conducted for other compounds and salts administered according to the present invention.

CHF 5074 levels in plasma and CSF may be measured by LC-MS/MS using a validated analytical method.

Plasma Aβ40 and Aβ42 concentrations as well as plasma sCD40L and Tumor Necrosis Factor-alpha (TNFα concentrations may be measured. Measurements of Aβ42, sCD40L, tau181P, total tau, and TNF-α in CSF may also be performed. Measurement of Aβ42 and tau CSF levels may have important clinical implications. MCI patients with both low Aβ42 and high tau levels had a substantially increased risk of developing AD, even after adjustment for confounding factors (see Hertze J, et al., *J. Alzheimers Dis.,* 21: 1119-1128 (2010), which is incorporated herein by reference in its entirety).

Expression of sCD40L is increased in microglial cells activated by β-amyloid (see Tan J, et al., *Science,* 286: 2352-2355 (1999), which is incorporated herein by reference in its entirety) and CSF levels of sCD40L have been proposed as biomarker of neuroinflammation induced by β-amyloid deposition (see Desideri G, et al., *Neurobiol, Aging*, 29: 348-356 (2008), which is incorporated herein by reference in its entirety).

Cognitive Tests.

The cognitive ability of the subjects may be assessed by means of one or more of the following neuropsychological tests. These tests may be administered at Screening, Baseline, and on Day 85 to explore the effects of different compounds, salts, and dose regimens on cognition. Both pencil and paper and computer based tests may be used. Tests may also be administered at the Screening assessment for familiarization purposes and to check that each participant is able to complete the tests (for example, that they do not have physical disabilities which limit their ability to use the touch screen). The Screening session may also ensure that any learning effects have taken place prior to Baseline assessment.

Pencil and Paper Tests.

Three well known pencil and paper tests highly vulnerable to brain dysfunction and sensitive to dementia may be administered to assess cognitive domains affected in the very early stages of AD.

The Digit Symbol Substitution Test (DSST) is a performance subtest of the Wechsler Adult Intelligence Scale-R (WAIS-R) (see Wechsler D., *The measurement of adult intelligence* ($3^{rd}$ ed.) Baltimore: Williams & Wilkins, 1944 and Wechsler D. *WAIS-R manual*, New York: Psychological corporation, 1981, both of which are incorporated herein by reference in their entireties). "It consists of four rows containing 100 small blank squares, each paired with a randomly assigned number from one to nine. Above these rows is a printed key that pairs each number with a different nonsense symbol. The task is to fill in the blank spaces with the symbol that is paired to the number above the blank space as quickly as possible for 90 seconds. Digit symbol is a test of psychomotor performance that is relatively unaffected by intellectual prowess, memory or learning. Digit symbol tends to be affected regardless of the locus of lesion. Its score is most likely to be depressed even when damage is minimal. This test is extremely sensitive to dementia, being one of the first tests to decline (see Storand M, et al., *Arch. Neurol.*, 46: 383-386 (1989), which is incorporated herein by reference in its entirety) and declines rapidly with disease progression (see Botwinick J, et al, *Arch. Neurol.*, 43: 1124-1127 (1986); Larrabee G J, et al., *J. Clin. Exp. Neuropsychol.*, 7: 497-504 (1985); and Lezak M D, *Neuropsychological assessment*, (third ed.), Oxford: Oxford University Press, 1995, pp. 376-380; all of which are incorporated herein by reference in their entireties). The score (point total) is the total number of squares filled in correctly.

The Trail Making Test-Part A and Part B (TMT-A and TMT-B) was part of the Army Individual Test Battery (see *Army Individual Test Battery. Manual of directions and scoring*, Washington, D.C.: War Department, Adjutant General's Office, 1944, which is incorporated herein by reference in its entirety) and it was added by Reitan to the Halstead Battery (see Reitan R M, *J. Cons. Psychol.*, 19: 393-394 (1955) and Reitan R M, *Percept Mot, Skills*, 8: 271-276 (1958), which is incorporated herein by reference in its entirety). Both parts of the Trail Making Test consist of 25 circles distributed over a sheet of paper. In Part A, the circles are numbered 1-25, and the patient should draw lines to connect the numbers in ascending order. In Part B, the circles include both numbers (1-13) and letters (A-L); as in Part A, the patient draws lines to connect the circles in an ascending pattern, but with the added task of alternating between the numbers and letters (i.e., 1-A-2-B-3-C, etc.). The patient is instructed to connect the circles as quickly as possible. "This is a test of complex visual scanning with a motor component. Like most other tests involving motor speed and attention functions, the TMT is highly vulnerable to the effects of brain injury (see Reitan R M, *Percept Mot. Skills*, 8: 271-276 (1958); Spreen O, et al., *J. Nerv. Ment. Dis.*, 140: 323-333 (1965); and Lezak M D, *Neuropsychological assessment*, (third ed.). Oxford: Oxford University Press, 1995, p. 382, all of which are incorporated herein by reference in their entireties). The test was found to be highly sensitive in patients with diffuse lesions (see Heilbronner R L, et al., *Arch. Clin. Neuropsychol.*, 6: 251-258 (1991), which is incorporated herein by reference in its entirety). "Part B is clearly the more sensitive part of the TMT" (see Spreen O, et al., *A compendium of neuropsychological tests. Administration, norms, and commentary*, Oxford: Oxford University Press, 1998, which is incorporated herein by reference in its entirety). Slow performance on part B probably points to "difficulties in complex-double or multiple-conceptual tracking." TMT can differentiate patients with mild AD from normal elderly subjects (see Storandt M, et al., *Arch. Neurol.*, 41: 497-499 (1984) and Lafleche G, et al. *Neuropsychology*, 9: 313-320 (1995), both of which are incorporated herein by reference in their entireties). Results for both TMT A and B are reported as the number of seconds required to complete the task; therefore, higher scores reveal greater impairment. Errors (pointed out immediately) affect the patient's score only in that the correction of errors is included in the completion time for the task.

The Hopkins Verbal Learning Test (HVLT) (see Brandt J., et al., *The Clinical Neuropsychologist*, 5: 125-142 (1991), which is incorporated herein by reference in its entirety) was designed as a relatively brief test of verbal learning and memory to be used when more comprehensive memory assessment is not feasible or when serial testing is desired. It is composed of 12 items, organized into three semantic categories, and presented over three consecutive learning trials. Twelve distracter items (6 semantically related and 6 semantically unrelated) are interspersed with the 12 test items during subsequent immediate yes/no recognition testing. The test includes three learning trials, a yes/no delayed recognition trial and a delayed recall trial (20-25 minute delay). The delayed recognition trial consists of a randomized list that includes the 12 target words and 12 nontarget words, six of which are drawn from the same semantic categories as the targets. In two cross-sectional studies, HVLT was effective in distinguishing mild demented and demented patients from healthy elderly controls (see Frank R M, et al., *Int. J. Geriatr. Psychiatry*, 15: 317-324 (2000) and Hogervorst E, et al., *Dement. Geriatr. Cogn. Disord.*, 13: 13-20 (2002), both of which are incorporated herein by reference in their entireties). Cases with MCI failed to benefit from repeated exposure to HVLT as compared with cognitively normal controls (see Schrijnemaekers A M, et al., *J. Clin. Exp. Neuropsychol.*, 28: 438-455 (2006), which is incorporated herein by reference in its entirety). Raw scores are derived for Total Recall, Delayed Recall, Retention (% retained), and a Recognition Discrimination Index. The score for this portion of the test is the number of list words correctly identified (hits) minus the number of nonlist words incorrectly identified (false alarms). Therefore, the actual score can range from −12 (no list words identified and all nonlist words identified) to +12 (all list words identified and no nonlist words identified)

Computer Based Tests.

One or more computer based cognitive tests from the Cambridge Neuropsychological Test Automated Battery (CANTAB) (see Robbins T W, et al., Dementia, 5: 266-281 (1994), which is incorporated herein by reference in its entirety) may be administered using a touch screen. These tests are sensitive to age-related cognitive decline and predictive of the development of Alzheimer's disease, suitable for use in older populations, and direct human equivalents of preclinical tests that have previously been shown to be improved by CHF 5074.

The Motor Control Task (MOT) is a brief exercise which familiarizes the participant with the touch screen system, at the start of each testing session. Participants touch a series of flashing crosses shown in different locations on the screen. This brief exercise is designed to familiarize participants with the touch screen interface. It can also identify any problems in vision, movement or comprehension that could affect performance. It takes approximately 3 minutes. Outcome measures: median latency and mean error.

The Pattern Recognition Memory (PRM) is a rapid human equivalent of the object recognition test that showed positive effects with CHF 5074 at the preclinical stage. The participant watches a series of 24 patterns appear, one at a time, on the screen. These patterns are designed so that they cannot be easily given verbal labels. In the recognition phase, the participant chooses which of two patterns they have seen before. This is then repeated with a new set of 24 patterns to be remembered. In the delayed recognition phase, administered 20 minutes after the second presentation phase, participants must again choose which of the patterns they have seen before. PRM performance can be enhanced in healthy volunteers using a variety of substances (see Randall D C, et al., Journal of Clinical Psychopharmacology, 25(2): 175-179 (2005) and Elsabagh S, et al., Psychopharmacology, 179: 437-446 (2005), both of which are incorporated herein by reference in their entireties). It takes approximately 7 minutes in total for both immediate and delayed phases. Outcome measures: immediate—percent correct, delayed—percent correct, immediate—median correct latency, delayed median correct latency.

The Paired Associates Learning (PAL) is an associative learning task that shows exceptional sensitivity to cognitive decline in normal aging and in the early stages of AD, and is predictive of later dementia in currently healthy older adults. In preclinical studies with CHF 5074, performance was significantly improved on fear conditioning, an associative learning task which, like PAL, is subserved by hippocampal function. PAL assesses visual associative learning and memory. Boxes are displayed on the screen and are automatically opened in a randomized order to show a number of patterns. Participants must learn to associate the patterns with locations on the screen. After all the boxes have been opened each pattern is then shown in the center of the screen and the participant must touch the box where that pattern was located. If the participant makes an error, the patterns are re-presented to remind the participant of their locations. The difficulty level increases with the number of patterns to be remembered. For participants who fail to complete all levels, an adjusted total is calculated that allows for errors predicted in the stages that were not attempted. Successful performance of the PAL test is dependent on functional integrity of the temporal lobe, particularly the hippocampus and entorhinal cortex (see Owen A M, et al., European Journal of Neuroscience, 8: 353-364 (1996) and Owen A M, et al., Neuropsychologia, 33: 1-24 (1995), both of which are incorporated herein by reference in their entireties). Performance on the PAL shows a distinctive age profile (see Blackwell A D, et al., "The effect of age, sex, and education on visuospatial paired associates learning ability: Preliminary data from a British population study," International Conference on Alzheimer's Disease; Honolulu, Hi., July 2010, which is incorporated herein by reference in its entirety). PAL performance can predict and measure cognitive decline in MCI and mild Alzheimer's disease, and can differentiate patients with AD from patients with depression, as well as healthy volunteers (see Fowler K S, et al., Journal of the International Neuropsychological Society, 3: 139-146 (1997); Fowler K. S., et al., Journal of the International Neuropsychological Society, 8: 58-71 (2002); Swainson R, et al., Dementia and Geriatric Cognitive Disorders, 12: 265-280 (2001); and Blackwell A D, et al., Dementia and Geriatric Cognitive Disorders, 17: 42-4 (2004), all of which are incorporated herein by reference in their entireties). PAL has sound preclinical validation and task performance is sensitive to pharmacological manipulation (see Taffe M A, et al., Psychopharmacology, 160: 253-262 (2002) and Greig N H, et al., Current Alzheimer Research, 2: 281-290 (2005), both of which are incorporated herein by reference in their entireties). It takes approximately 7 minutes. Outcome measures: total errors (adjusted), first trial memory score, number of patterns reached.

The Spatial Working Memory (SWM) is a measure of prefrontal function equivalent to the Morris water maze, which showed marginal effects of CHF 5074 at the preclinical study. SWM measures the ability to retain spatial information and manipulate it in working memory. It is a self-ordered task that also assesses the use of strategy. Participants must search for blue tokens by touching the colored boxes to open them. The task becomes more difficult as the number of boxes increases. The critical instruction is that the participant must not return to a box where a token has previously been found. SWM task performance depends on integrity of the prefrontal cortex. Performance is impaired by damage to the dorsolateral prefrontal cortex (see Owen A M, et al., Neuropsychologia, 28(10): 1021-1034 (1990) and Manes F, et al., Brain, 125, 624-639 (2002), both of which are incorporated herein by reference in their entireties), and in neuroimaging studies in healthy volunteers, performance is associated with activation in the dorsolateral and mid ventrolateral prefrontal cortex (see Owen A M, et al., European Journal of Neuroscience, 8, 353-364 (1996), which is incorporated herein by reference in its entirety). SWM performance is significantly impaired in mild-moderate AD (see Sahgal A, et al., International Journal of Geriatric Psychiatry, 7, 427-436 (1992), which is incorporated herein by reference in its entirety). SWM is sensitive to differential effects of pharmacological compounds (see Mehta M A, et al., Journal of Neuroscience, 20 RC65, 1-6 (2000); Mehta M A, et al., Journal of Child Psychology and Psychiatry, 45: 293-305 (2004); Kempton S, et al., Psychological Medicine, 29: 527-538 (1999); and Turner D C, et al., Psychopharmacology, 178(2-3): 286-295 (2005), all of which are incorporated herein by reference in their entireties). It takes approximately 7 minutes. Outcome measures: between errors 4-10 boxes, strategy 6-10 boxes.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the treatment of mild cognitive impairment comprising administering, to a subject in need thereof, an effective amount of
1-(3',4'-dichloro-2-fluorobiphenyl-4-yl)cyclopropanecarboxylic acid or
a pharmaceutically acceptable salt thereof or ester thereof,
wherein said subject carries the gene expressing the apolipoprotein APOE4, and
wherein said subject is of an age between 45 and 65 years.

2. A method according to claim 1, wherein said 1-(3',4'-dichloro-2-fluorobiphenyl-4-yl)cyclopropanecarboxylic acid, pharmaceutically acceptable salt thereof, or ester thereof is administered orally.

3. A method according to claim 1, wherein said 1-(3',4'-dichloro-2-fluorobiphenyl-4-yl)cyclopropanecarboxylic acid, pharmaceutically acceptable salt thereof, or ester thereof is administered in an amount of 1 mg to 2000 mg per day.

4. A method according to claim 2, wherein said 1-(3',4'-dichloro-2-fluorobiphenyl-4-yl)cyclopropanecarboxylic acid, pharmaceutically acceptable salt thereof, or ester thereof is administered in an amount of 1 mg to 2000 mg per day.

5. A method according to claim 1, wherein said 1-(3',4'-dichloro-2-fluorobiphenyl-4-yl)cyclopropanecarboxylic acid, pharmaceutically acceptable salt thereof, or ester thereof is administered in an amount of 100 mg to 800 mg per day.

6. A method according to claim 2, wherein said 1-(3',4'-dichloro-2-fluorobiphenyl-4-yl)cyclopropanecarboxylic acid, pharmaceutically acceptable salt thereof, or ester thereof is administered in an amount of 100 mg to 800 mg per day.

7. A method according to claim 1, wherein said 1-(3',4'-dichloro-2-fluorobiphenyl-4-yl)cyclopropanecarboxylic acid, pharmaceutically acceptable salt thereof, or ester thereof is administered in an amount of 200 mg to 600 mg per day.

8. A method according to claim 2, wherein said 1-(3',4'-dichloro-2-fluorobiphenyl-4-yl)cyclopropanecarboxylic acid, pharmaceutically acceptable salt thereof, or ester thereof is administered in an amount of 200 mg to 600 mg per day.

* * * * *